United States Patent
Asbaghi (10) Patent No.: US 6,530,905 B2
(45) Date of Patent: Mar. 11, 2003

(54) SELF-SHEATHING DENTAL NEEDLE

(75) Inventor: Hooman A. Asbaghi, Del Mar, CA (US)

(73) Assignee: HBA Medical Group, Inc., Las Vegas, NV (US)

(*) Notice: Subject to any disclaimer, the term of this patent is extended or adjusted under 35 U.S.C. 154(b) by 38 days.

(21) Appl. No.: 09/775,239

(22) Filed: Feb. 1, 2001

(65) Prior Publication Data

US 2002/0103461 A1 Aug. 1, 2002

(51) Int. Cl.$^7$ ................................ A61M 5/32
(52) U.S. Cl. ...................... 604/198; 604/218
(58) Field of Search ................ 604/198, 218, 604/195

(56) References Cited

U.S. PATENT DOCUMENTS

| | | | |
|---|---|---|---|
| 5,037,402 A | 8/1991 | Bartman | |
| 5,156,596 A | 10/1992 | Balbierz | |
| 5,222,945 A | * 6/1993 | Basnight | 604/198 |
| 5,232,457 A | * 8/1993 | Grim | 604/198 |
| 5,242,401 A | 9/1993 | Colsky | |
| 5,267,977 A | 12/1993 | Feeney | |
| 5,295,975 A | 3/1994 | Lockwood | |
| 5,324,265 A | * 6/1994 | Murray et al. | 604/195 |
| 5,346,480 A | * 9/1994 | Hess et al. | 604/218 |
| 5,376,080 A | 12/1994 | Petrussa | |
| 5,389,085 A | 2/1995 | D'Alessio | |
| 5,403,286 A | 4/1995 | Lockwood | |
| 5,591,138 A | * 1/1997 | Vaillancourt | 604/198 |
| 5,695,475 A | * 12/1997 | Best, Jr. et al. | 604/218 |

\* cited by examiner

*Primary Examiner*—Philippe Derakshani
(74) *Attorney, Agent, or Firm*—Nydegger & Associates (57) ABSTRACT

A self-sheathing dental needle includes a finger grip slideably mounted to a syringe body and a plunger to expel a fluid medicament from the syringe body. The finger grip is formed with a tang that is positioned near the distal end of the syringe body when the finger grip is fully advanced in the distal direction. A needle cartridge is provided having a needle mounted in a needle holder, a sheath slideably mounted to the needle holder, and a lock body for locking the sheath in position over the distal end of the needle. When the cartridge is attached to the syringe body and aligned, the lock body can be reconfigured to release the sheath for movement relative to the needle. Specifically, the finger grip can be translated to cause the tang to engage the lock body, release the sheath, and expose the distal end of the needle.

20 Claims, 5 Drawing Sheets

SELF-SHEATHING DENTAL NEEDLE

FIELD OF THE INVENTION

The present invention pertains generally to syringes for medical use. More particularly, the present invention pertains to syringes having a self-sheathing needle. The present invention is particularly, but not exclusively, useful for syringes having a safety sheath that can be releasably locked over the tip of the syringe needle.

BACKGROUND OF THE INVENTION

The American Dental Association (ADA) attributes most needlestick and subsequent infections in dental offices to the handling of sharp instruments and needles which must be handled carefully to prevent injuries and recapped after use. If a patient requires multiple injections from a single syringe, the needle should be recapped between each use to preclude the possibility of needlestick injury. At best, needles may be recapped by placing the cap in a special holder, by using forceps or other appropriate instrument to grasp the cap, or by simply laying the cap on the instrument tray and then manually guiding the needle into the cap until it is completely sealed. The greatest risk of needlestick injury occurs when the cap must be manually placed over the used needle. Almost 90% of needlestick injuries occur either when the operator withdraws the needle from the patient, or between injections. Operators usually do not bother to take the time to re-cap the needle between injections, and leave the bare infected needle uncovered on the tray, and this is precisely when accidents occur.

The lack of passive devices specifically designed for injury prevention has shown itself to be one of the greatest obstacles in preventing operator exposure to infected blood and bodily fluids. According to a clinical report published in the September 1997 issue of JADA, during a 63-month period, in which 423 parenteral exposures to blood and bodily fluids were documented, dental students and dental assistants had the highest rate of exposure; syringe needle injuries were the most common type of exposure; and giving injections, cleaning instruments after procedures and drilling were the activities most frequently associated with exposure. According to a study published in the July 1998 report of the CDC, 17% of all needlestick injuries to New York City healthcare workers occurred among dental workers, and 10%–18% of these latter injuries resulted in HB infection.

In light of the above, it is an object of the present invention to provide devices suitable for the purposes of injecting a medicament in a safe, efficient manner. It is another object of the present invention to provide a syringe having a disposable needle cartridge that remains in a locked guarded configuration until engagement with a syringe body. It is yet another object of the present invention to provide a syringe that passively resheaths and locks after use. It is yet another object of the present invention to provide a self-sheathing needle cartridge that can be used in conjunction with a re-useable syringe body and a standard medicament cartridge. Yet another object of the present invention is to provide a self-sheathing dental needle which is easy to use, relatively simple to manufacture, and comparatively cost effective.

SUMMARY OF THE PREFERRED EMBODIMENTS

The present invention is directed to a self-sheathing dental needle and a method for using a self-sheathing dental needle. For the present invention, the dental needle includes a cylindrically shaped syringe body that surrounds a chamber and defines a cylinder axis. The chamber is open at both its distal and proximal ends and the syringe body is formed with an exterior surface. A first finger grip is permanently affixed to the exterior surface of the syringe body near the proximal end. Further, the chamber is sized to hold a medication cartridge with an adequate amount of fluid medicament. A plunger is provided for insertion into the proximal end of the syringe body and for engagement with the medication cartridge to apply a force upon the fluid medicament in the medication cartridge.

In addition to the first finger grip, a second finger grip is slideably mounted on the exterior surface of the syringe body. Specifically, the second finger grip is oriented to allow the second finger grip to move relative to the syringe body in a direction that is parallel to the cylinder axis. Preferably, the second finger grip includes a curved proximal portion for engagement with a finger, a distal tang, and a substantially straight section connecting the curved portion to the tang. When the second finger grip is fully advanced in the distal direction, the tang is positioned near the distal end of the syringe body. Additionally, a portion of the tang extends outwardly in a radial direction from the cylinder axis. A spring that is mounted on the syringe body biases the second finger grip in the distal direction.

The self-sheathing dental needle of the present invention also includes a needle cartridge that is engageable with the syringe body. Specifically, the needle cartridge includes two parallel offset needle sections with an interconnecting midsection that provides for fluid communication between the sections. A first needle section is formed with an end extending in the distal direction from the midsection, and the second needle section is formed with an end extending in the proximal direction.

The midsection of the needle is encased in a needle holder to rigidly attach the needle to the needle holder. The needle holder includes a cylindrically shaped section positioned over the second section of the needle and centered on the second axis. For the present invention, the cylindrical section of the needle holder extends beyond the second section of the needle in the proximal direction to guard the end of the second section of the needle. Additionally, the diameter of the cylindrical section is sized to fit over the distal end of the syringe body and create a tight seal between the syringe body and the cylindrical section when the needle cartridge is engaged with the syringe body. The needle cartridge further includes a sheath that is disposed over the first section of the needle and slideably mounted on the needle holder. Preferably, the sheath is substantially shaped as an elongated cylinder having a lumen. Specifically, the sheath is centered on the first axis and slideably mounted on the holder to allow the sheath to move relative to the holder and in the direction of the first axis. For this purpose, the sheath is disposed within a hole provided in the holder. A guide can be mounted on the needle and disposed within the lumen of the sheath to maintain the sheath centered on the first axis. The midsection of the needle passes through a slit in the sheath. Preferably, the slit extends axially along the sheath to allow the sheath to move relative to the needle.

The needle cartridge further includes a spring enclosure that is mounted to the needle holder. Preferably, the spring enclosure is substantially cylindrically shaped and mounted on the needle holder proximal to the second section of the needle and centered on the first axis. The distal end of the spring enclosure is open, while the proximal end is closed. As such, a coil spring can be disposed within the spring enclosure for compression between the sheath and the proximal end of the spring enclosure. With this cooperation of structure, the coil spring in the spring enclosure biases the sheath in the distal direction. Preferably, the inner diameter of the spring enclosure is of sufficient size to allow the sheath to travel within the spring enclosure.

An important aspect of the present invention is a lock that forms a part of the cartridge. For the present invention, the lock is formed with a lock body having a distal end for attachment to the proximal end of the sheath, and a proximal end that engages the distal end of the coil spring in the spring enclosure. The lock body is sized relative to the inner diameter of the spring enclosure to allow the lock body to travel within the spring enclosure.

A locking tab extends radially from the lock body to create a hinged connection between the locking tab and lock body. As such, the locking tab is moveable between a locking configuration in which the tab is in an unstressed state and extends away from the first axis, and a release configuration in which the tab is biased to a position where the tab is relatively closer to the first axis. Thus, upon the application of an appropriate force, the tab can be moved from the locking configuration to the release configuration, and upon release of the applied force the tab will attempt to return to the locking configuration.

When the locking tab is in the locking configuration, translation of the lock body and sheath relative to the needle is blocked. Specifically, the locking tab abuts against the distal edge of the spring enclosure to thereby limit proximal motion by the sheath and lock body relative to the needle. Additionally, the lock body is preferably sized to be larger than the hole formed in the needle holder. As such, the lock body abuts against the needle holder to prohibit distal motion by the sheath and lock body relative to the needle, when the locking tab is positioned distal to the spring enclosure.

The locking tab is formed with a cam surface for the purpose of reconfiguring the locking tab from the locking configuration to the release configuration. The cam surface is formed on the distal side of the locking tab and oriented at an angle to the first axis. As such, a force directed parallel to the first axis can be applied to the cam surface to reconfigure the locking tab from the locking configuration and into the release configuration.

To assemble and use the self-sheathing dental needle, first the fluid medicament and plunger are inserted into the chamber of the syringe body. Next, the second finger grip is advanced in the distal direction relative to the syringe body until the tang is positioned near the distal end of the syringe body. At this point, the syringe body is prepared for engagement with a needle cartridge. For this purpose, a needle cartridge as described above that includes a needle, needle holder, sheath, guide, spring enclosure, spring, lock body and locking tab is prepared with the locking tab in the lock configuration. As such, the sheath is positioned to extend distally over the end of the first section of the needle to guard against accidental needle sticks.

Once the syringe body and needle cartridge have been prepared for engagement, the distal end of the syringe body can be inserted into the cylindrical portion of the needle holder to create a tight seal between the holder and syringe body. As such, the end of the second section of the needle will be positioned in fluid communication with the chamber of the syringe body. If a medicament cartridge is used, the second section of the needle and the medicament cartridge can be adequately sized to ensure that the end of the second section of the needle penetrates the medicament cartridge when the syringe body is inserted into the needle holder.

To unlock the sheath, the cartridge is first rotated about the cylinder axis relative to the syringe body to align the tang of the second finger grip with the locking tab. Specifically, the cartridge is rotated to position the tang adjacent to the cam surface of the locking tab. This rotation will result in the tang being positioned distal to the locking tab. Next, the second finger grip can be slid in the proximal direction relative to the syringe body. Upon initial movement of the second finger grip, the tang is caused to contact the cam surface of the locking tab and bias the locking tab into the release configuration. In the release configuration, the locking tab is no longer blocked by the spring enclosure, and accordingly, the sheath and lock body are able to translate in the proximal direction relative to the needle.

Continued movement of the second finger grip in the proximal direction causes the tang to engage the locking tab and pull the lock body and sheath in the proximal direction. The spring enclosure is formed with an axial slit to allow the tang to remain in contact with the locking tab as the second finger grip pulls the lock body and a portion of the sheath into the spring enclosure. This proximal movement by the second finger grip, sheath and lock body will be resisted by the spring on the syringe body and the spring in the spring enclosure. Eventually, movement of the second finger grip in the proximal direction will be stopped by the syringe body, leaving the second finger grip positioned directly opposite the syringe body from the first finger grip. When the second finger grip is moved to this position, the sheath retracts over the first section of the needle to expose the end of the first section of the needle. Only the spring in the spring enclosure prevents further retraction of the sheath.

With the end of the first section of the needle exposed, the user can insert the end of the needle into a patient for an injection. Needle penetration depth is not limited to the exposed portion of the needle because the sheath is able to retract as the user applies force to the syringe to press the needle into the patient. At this point, only the spring in the spring enclosure resists the retraction of the sheath. To inject the patient with the fluid medicament, the plunger is depressed into the chamber of the syringe body to expel medication from the chamber, through the needle and into the patient. For this purpose, the finger grips can be used to offset the force required to depress the plunger into the chamber.

When the needle is removed from the patient, the spring in the spring enclosure expands to force the sheath to return to the position where only a portion of the needle is exposed. At this point, the user can give the patient another injection or release the second finger grip to fully cover the first section of the needle by the sheath. Specifically, upon release of the second finger grip, the spring mounted on the syringe body will further expand to translate the second finger grip, lock body and sheath distally until the lock body abuts against the needle holder. This distal movement of the lock body will cause the locking tab to move to a position distal to the edge of the spring enclosure, reconfiguring the locking tab back into the locking configuration from the release configuration and repositioning the sheath over the end of the first section of the needle. At this point, relative movement between the sheath and the needle is blocked by the locking tab (i.e. the sheath will be locked in position over the end of the first section of the needle). Once the sheath is safely locked over the end of the first section of the needle, the syringe can be stored safely for later use or the needle cartridge can be removed from the syringe body and discarded. Upon removal of the needle cartridge, the syringe body can be autoclaved for reuse.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
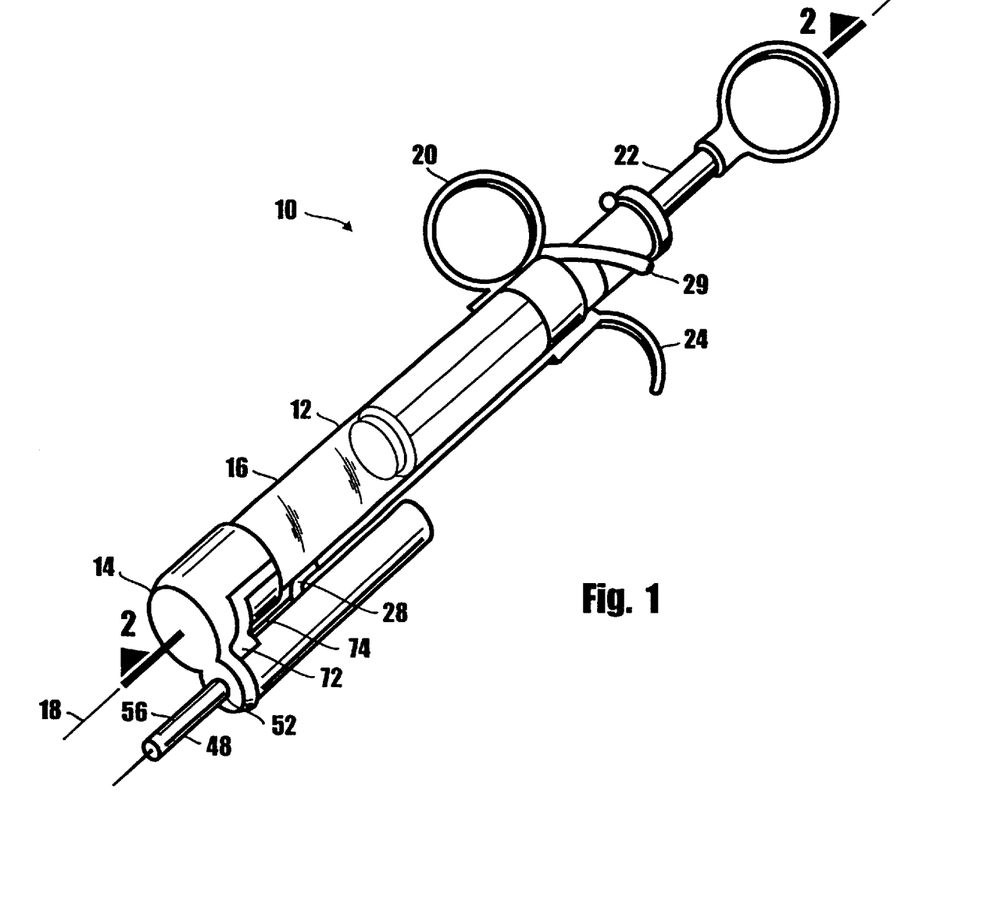
FIG. 1 is a perspective view of a self-sheathing dental needle in accordance with the present invention, shown with the sheath partially retracted to expose a portion of the needle.

Referring to FIG. 1, a self-sheathing dental needle in accordance with the present invention is shown and generally designated 10. As shown in FIG. 1, the system includes a syringe body 12 and a needle cartridge 14. Preferably, as shown, the syringe body 12 is cylindrically shaped, surrounds a chamber 16, and defines a cylinder axis 18. For the present invention, a finger grip 20 is permanently affixed to the exterior surface of the syringe body 12 near the proximal end. A plunger 22 is provided for insertion into the proximal end of the syringe body 12 to expel fluid from the chamber 16.

Figure 2:
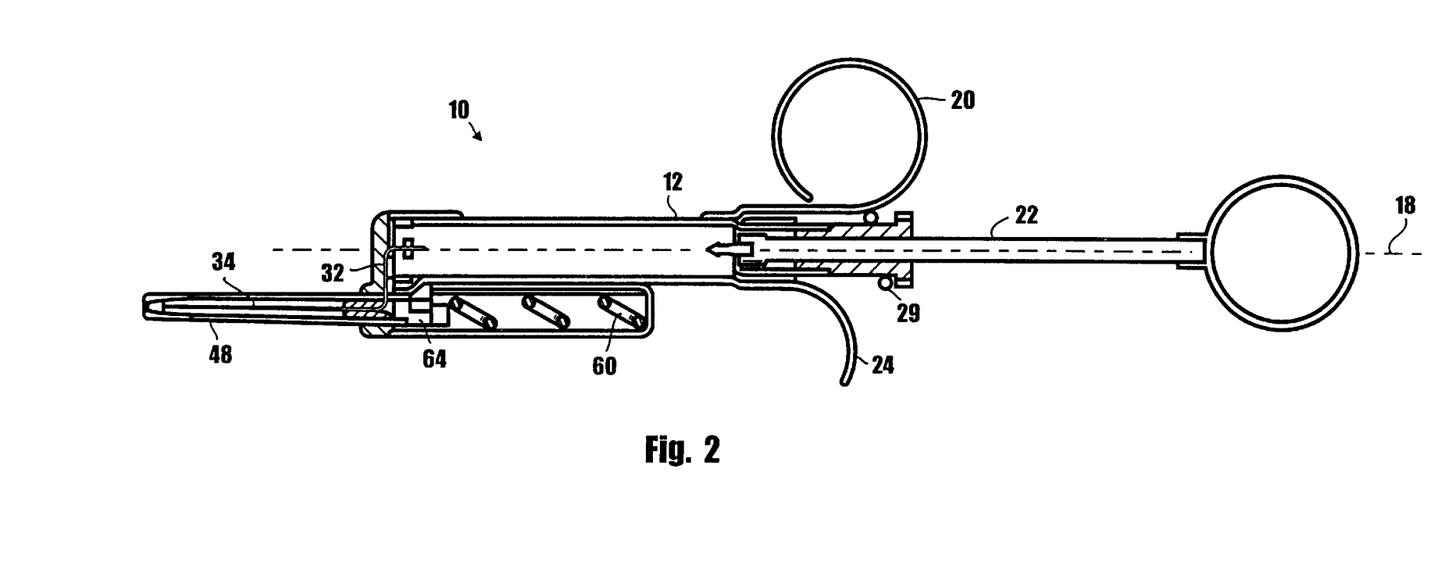
FIG. 2 is a cross sectional view of the self-sheathing dental needle as seen along line 2—2 in FIG. 1, shown with the sheath locked in position over the needle.
Figure 3:
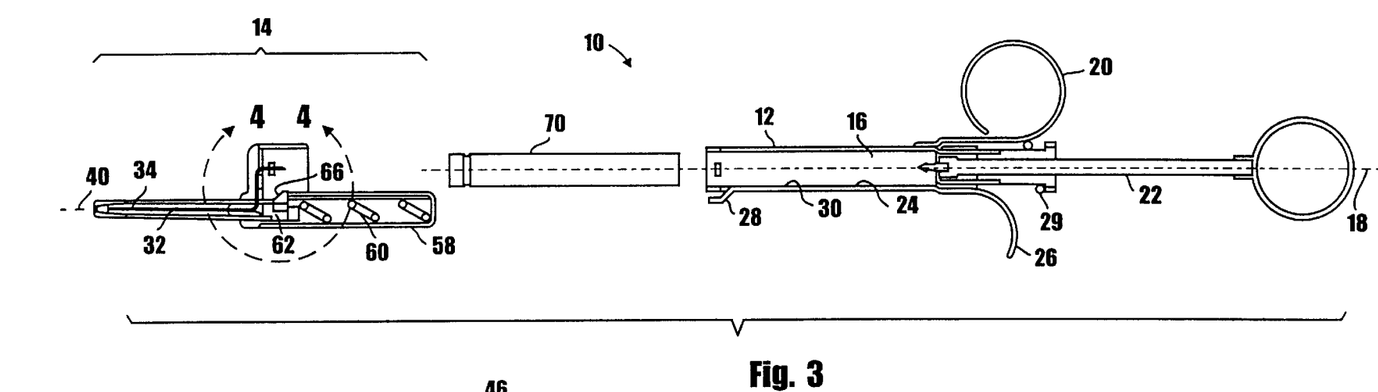
FIG. 3 is an exploded cross sectional view of the self-sheathing dental needle as seen in FIG. 2.

With cross reference to FIGS. 1 and 2, it can be seen that a second finger grip 24 is slideably mounted on the exterior surface of the syringe body 12 and oriented to allow the finger grip 24 to move relative to the syringe body 12 in a direction that is parallel to the cylinder axis 18. As shown in FIG. 3, the finger grip 24 includes a curved proximal portion 26 for engagement with the user's finger, a distal tang 28, and a substantially straight section 30 connecting the curved portion 26 to the tang 28. In accordance with the present invention, the finger grip 24 can be advanced in the distal direction until the tang 28 is positioned near the distal end of the syringe body 12. Additionally, as shown, a portion of the tang 28 extends in a radial direction from the cylinder axis 18. A spring 29 is mounted on the syringe body 12 to bias the finger grip 24 in the distal direction. Preferably, the syringe body 12, spring 29, finger grips 20, 24 and plunger 22 are made from rigid metallic materials suitable for autoclaving and reuse.

Figure 4:
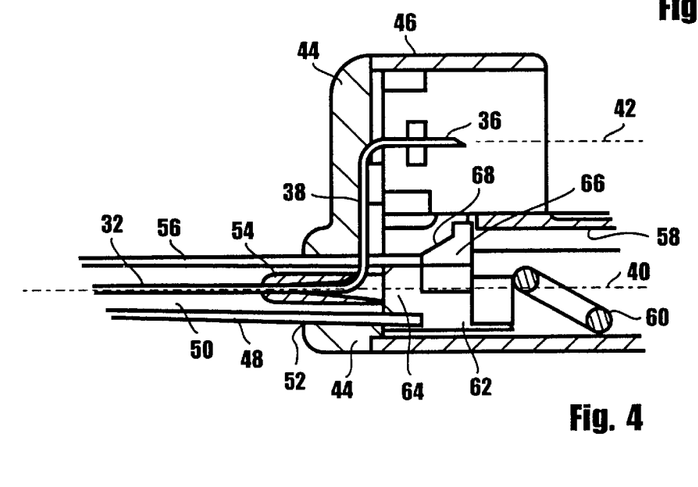
FIG. 4 is an enlarged view of a portion of the self-sheathing dental needle as enclosed by line 4 in FIG. 3.

Referring now with cross reference to FIGS. 3 and 4, a needle cartridge 14 is provided for engagement with the syringe body 12. As shown, the needle cartridge 14 includes a needle 32 having a first section 34 extending in the distal direction and a second section 36 extending in the proximal direction. A midsection 38 connects the first section 34 to the second section 36. Further shown, the first section 34 of the needle 32 extends substantially along a first axis 40 and the second section 36 of the needle 32 extends substantially along a second axis 42. Preferably, as shown, the first axis 40 is parallel to the second axis 42 and distanced therefrom.

In accordance with the present invention, the midsection of the needle 32 is encased in a needle holder 44 to rigidly attach the needle 32 to the needle holder 44. Preferably, the needle holder 44 is constructed of plastic and includes a cylindrically shaped section 46 positioned over the second section 36 of the needle 32 and centered on the second axis 42. As further shown in FIGS. 3 and 4, the cylindrical section 46 of the needle holder 44 extends beyond the end of the second section 36 of the needle 32 in the proximal direction to guard the end of the second section 36 of the needle 32. Additionally, the cylindrical section 46 is sized to fit over the distal end of the syringe body 12 and create a tight seal between the syringe body 12 and the needle holder 44.

Important for the present invention, the needle cartridge 14 includes a sheath 48 that is disposed over the end of the first section 34 of the needle 32 and slideably mounted on the needle holder 44. Preferably, as shown, the sheath 48 is substantially shaped as an elongated cylinder having a lumen 50. Specifically, the sheath 48 is centered on the first axis 40 and slideably mounted on the needle holder 44 to allow the sheath 48 to move in the direction of the first axis 40, relative to the needle holder 44. For this purpose, the sheath 48 is disposed within a hole 52 (also shown in FIG. 1) provided in the needle holder 44. An optional guide 54 can be mounted on the needle 32 and disposed within the lumen 50 of the sheath 48 to maintain the sheath 48 centered on the first axis 40. A slit 56 extends axially along the sheath 48 to allow the sheath 48 to move relative to the needle 32.

Referring still to FIGS. 3 and 4, the needle cartridge 14 further includes a spring enclosure 58 that is attached to the needle holder 44. Preferably, the spring enclosure 58 is cylindrically shaped and mounted on the needle holder 44 proximal to the second section 36 of the needle 32 and centered on the first axis 40. As shown, the distal end of the spring enclosure 58 is open, while the proximal end is closed. As such, a coil spring 60 can be disposed within the spring enclosure 58 for compression between the sheath 48 and the proximal end of the spring enclosure 58. With this cooperation of structure, the spring 60 biases the sheath 48 in the distal direction. Preferably, as shown, the spring enclosure 58 is sized to allow the sheath 48 to travel within the spring enclosure 58. It is to be appreciated that the coil spring 60 and spring enclosure 58 can be replaced with other mechanisms known in the pertinent art for biasing the sheath 48 in the distal direction.

Referring still to FIGS. 3 and 4, a lock 62 is provided that forms a part of the needle cartridge 14. Preferably, the lock 62 is formed with lock body 64 having a distal end for attachment to the proximal end of the sheath 48, and a proximal end that engages the distal end of the spring 60. As further shown, in the preferred embodiment for the present invention, the lock body 64 is sized relative to the inner diameter of the spring enclosure 58 to allow the lock body 64 to travel within the spring enclosure 58. Additionally, a locking tab 66 extends radially from the lock body 64 to create a hinged connection between the locking tab 66 and the lock body 64. As such, the locking tab 66 is moveable between a locking configuration (shown in FIG. 2) in which the tab 66 is in an unstressed state and extends away from the first axis 40, and a release configuration (shown in FIG. 5A) in which the locking tab 66 is biased to a position that is relatively closer to the first axis 40 than when the tab is in the locking configuration. Thus, upon the application of an appropriate force, the locking tab 66 can be moved from the locking configuration to the release configuration and upon release of the force the locking tab 66 will attempt to return to the locking configuration.

Referring now to FIG. 3, the locking tab 66 is shown positioned in the locking configuration. In this configuration, travel by the lock body 64 and sheath 48 relative to the needle 32 is blocked. Specifically, the locking tab 66 abuts against the distal edge of the spring enclosure 58 to thereby limit proximal motion by the sheath 48 and lock body 64 relative to the needle 32. Additionally, in the preferred embodiment for the present invention, the lock body 64 is sized to be larger than the hole 52 formed in the needle holder 44. With this combination of structure, the lock body 64 abuts against the needle holder 44 when the locking tab 66 is positioned in the locking configuration. As such, distal motion by the sheath 48 and lock body 64 relative to the needle 32 is prohibited when the locking tab 66 is positioned in the locking configuration.

As best shown in FIG. 4, the locking tab 66 is formed with a cam surface 68 for the purpose of reconfiguring the locking tab 66 from the locking configuration to the release configuration. As shown, the cam surface 68 is formed on the distal side of the locking tab 66 and oriented at an angle to the second axis 42. As such, a force directed parallel to the second axis 42 can be applied to the cam surface 68 to reconfigure the locking tab 66 from the locking configuration into the release configuration.

Referring back to FIG. 3, an exploded view of the syringe components is shown with the components positioned for assembly of the self-sheathing dental needle 10. It is to be appreciated, with reference to FIG. 3, that a fluid medicament (which may be housed in an optional medicament cartridge 70, as shown) and the plunger 22 can be inserted into the chamber 16 of the syringe body 12. Next, the finger grip 24 is advanced in the distal direction relative to the syringe body 12 until the tang 28 extends near the distal end of the syringe body 12. At this point, the syringe body 12 is prepared for engagement with the needle cartridge 14. For this purpose, the needle cartridge 14, as described above and shown in FIGS. 3 and 4 having a needle 32, needle holder 44, sheath 48, guide 54, spring enclosure 58, spring 60, lock body 64 and locking tab 66, is prepared with the locking tab 66 in the locking configuration. In this configuration, the sheath 48 extends distally over the end of the first section 34 of the needle 32 to guard against accidental needle sticks.

Referring now with cross reference to FIGS. 1, 2, 3 and 4, it is to be appreciated that once the syringe body 12 and needle cartridge 14 have been prepared for engagement, the distal end of the syringe body 12 can be inserted into the cylindrical section 46 of the needle holder 44 to create a tight seal between the needle holder 44 and syringe body 12. As such, the end of the second section 36 of the needle 32 will be in fluid communication with the chamber 16 of the syringe body 12. As shown, the medicament cartridge 70 and the second section 36 of the needle 32 can be adequately sized to ensure that the second section 36 of the needle 32 pierces the medicament cartridge 70 when the syringe body 12 is inserted into the needle holder 44.

To unlock the sheath 48 for an injection, the cartridge 14 is first rotated about the cylinder axis 18 relative to the syringe body 12 to align the tang 28 of the finger grip 24 and the locking tab 66. An opening 72 in the needle cartridge 14 (shown in FIG. 1) allows the tang 28 to enter the needle cartridge 14 and assume a position adjacent and distal to the cam surface 68 of the locking tab 66 when the cartridge 14 is rotated about the cylinder axis 18 (This configuration is shown in FIG. 2).

Figure 5A:
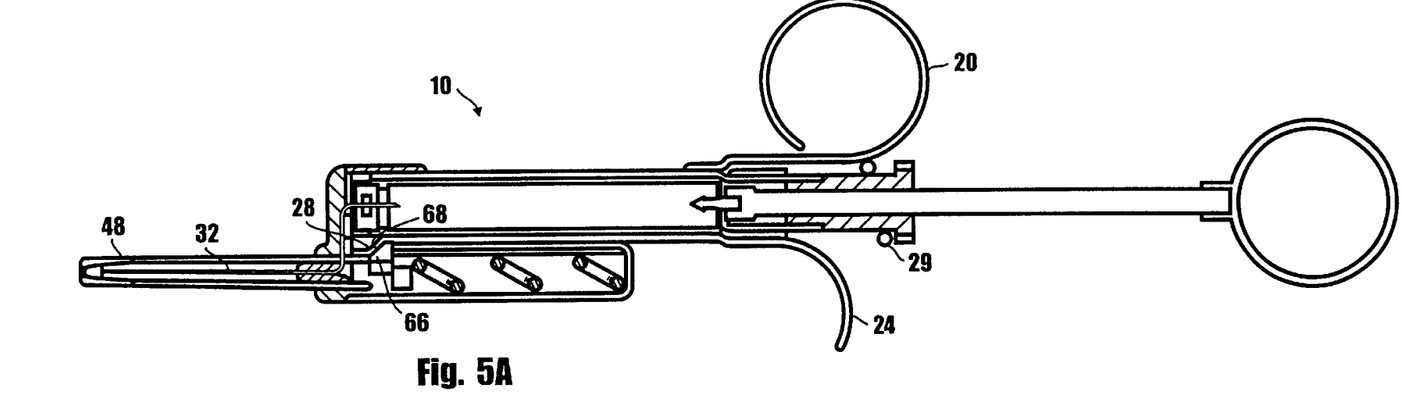
FIG. 5A is a cross sectional view of the self-sheathing dental needle as in FIG. 2, showing the self-sheathing dental needle after the second finger grip has been moved in the proximal direction to bias the locking tab into a configuration where the locking tab clears the spring enclosure.

Referring now with cross reference to FIGS. 2 and 5A, it is to be appreciated that the finger grip 24 can be slid in the proximal direction relative to the syringe body 12 to unlock the sheath 48. Specifically, FIG. 5A shows the self-sheathing dental needle 10 after initial movement of the finger grip 24 has caused the tang 28 to contact the cam surface 68 of the locking tab 66 and bias the locking tab 66 into the release configuration. As shown, in the release configuration, the locking tab 66 is no longer blocked by the spring enclosure 58, and accordingly, the sheath 48 and lock body 64 are able to translate relative to the needle 32.

Figure 5B:
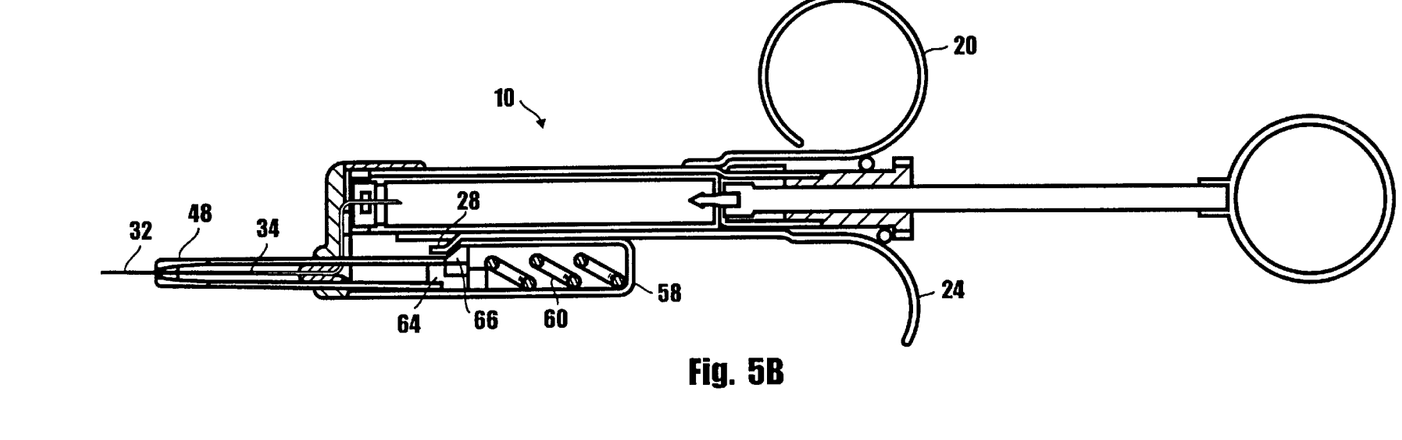
FIG. 5B is a cross sectional view of the self-sheathing dental needle as in FIG. 2, showing the self-sheathing dental needle after the second finger grip has been fully translated in the proximal direction to expose a portion of the first section of the needle.

Referring now with cross reference to FIGS. 5A and 5B, it is to be appreciated that once the locking tab 66 is in the release configuration (i.e. FIG. 5A), further movement of the finger grip 24 in the proximal direction causes the tang 28 to engage the locking tab 66 and pull the lock body 64 and sheath 48 in the proximal direction (as shown in FIG. 5B). An axial slit 74 in the spring enclosure 58 (shown in FIG. 1) is provided to allow the tang 28 to maintain contact with the locking tab 66 during translation of the finger grip 24. This proximal movement by the sheath 48 and lock body 64 will be resisted by the springs 29, 60. Eventually, the movement of the finger grip 24 in the proximal direction will be stopped by the syringe body 12, leaving the finger grip 24 positioned directly opposite the syringe body 12 from the finger grip 20, as shown in FIG. 5B. When the finger grip 24 is moved to this position (i.e. FIG. 5B), the sheath 48 retracts over the needle 32 to expose a portion of the first section 34 of the needle 32. As shown, only the spring 60 prevents further retraction of the sheath 48.

Figure 5C:
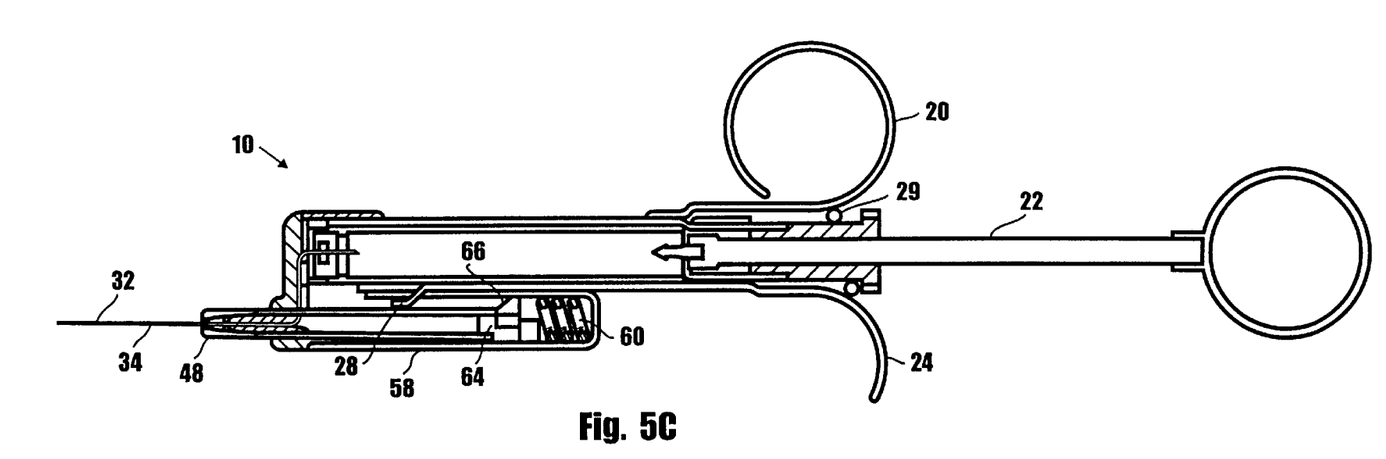
FIG. 5C is a cross sectional view of the self-sheathing dental needle as in FIG. 2, showing the self-sheathing dental needle with the sheath fully retracted.

Referring now with cross reference to FIGS. 5B and 5C, it is to be appreciated that once the end of the first section 34 of the needle 32 is exposed, the sheath 48 is free to translate in the proximal direction relative to the needle 32, with only the spring 60 resisting the further retraction of the sheath 48. Thus, the user (not shown) can insert the first section 34 of the needle 32 into a patient (also not shown) for an injection. It is to be appreciated that the depth of penetration of the needle 32 is not limited by the sheath 48 because the sheath 48 is able to retract as the user presses the needle 32 into the patient. For the present invention, a low force coil spring can be used as the spring 60 to ensure that only a light pressure is applied to the patient's gums or skin by the sheath 48.

Figure 5D:
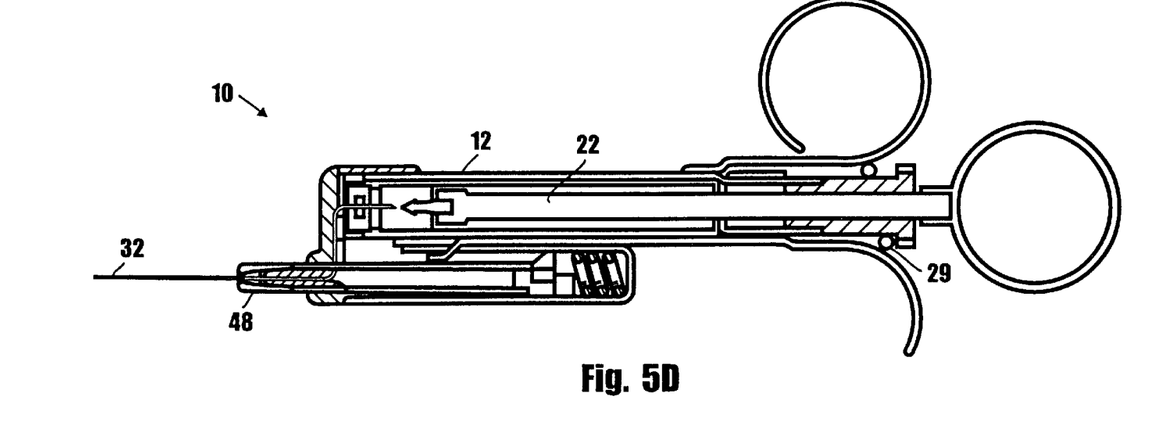
FIG. 5D is a cross sectional view of the self-sheathing dental needle as in FIG. 2, showing the self-sheathing dental needle with the sheath fully retracted and the plunger depressed.

Referring now with cross reference to FIGS. 5C and 5D, it is to be appreciated that the self-sheathing dental needle 10 can be used to inject the patient with the fluid medicament by depressing the plunger 22 into the chamber 16 of the syringe body 12 to expel medication from the chamber 16, through the needle 32 and into the patient. For this purpose, the finger grips 20, 24 can be used to offset the force required to depress the plunger 22.

When the needle 32 is withdrawn from the patient, the spring 60 provides the force necessary to return the sheath 48 back to the position where only a portion of the needle 32 is exposed (i.e. FIG. 5B). At this point, the user can give the patient another injection or release the finger grip 24 to fully cover the first section 34 of the needle 32 by the sheath 48 (i.e. FIG. 2). Specifically, upon release of the finger grip 24, the springs 29, 60 will expand to translate the finger grip 24, lock body 64 and sheath 48 distally until the lock body 64 abuts against the needle holder 44 (i.e. the configuration shown in FIG. 2). This distal translation of the lock body 64 relative to the needle 32 will cause the locking tab 66 to move to a position distal to the edge of the spring enclosure 58 and reconfigure from the release configuration to the locking configuration. In this configuration, as shown in FIG. 2, the first section 34 of the needle 32 is fully covered by the sheath 48, and relative movement between the sheath 48 and the needle 32 is blocked by the locking tab 66 (i.e. the sheath 48 is locked in position over the first section 34 of the needle 32). Once the sheath 48 is safely locked over the first section 34 of the needle 32, the needle cartridge 14 can be removed from the syringe body 12 and discarded along with the empty medication cartridge 70. The syringe body 12, including the spring 29, finger grips 20, 24 and the plunger 22, can be autoclaved for reuse.

While the particular Self-Sheathing Dental Needle as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A syringe which comprises:
   a syringe body having a chamber for holding a fluid medication;
   a needle having a first end and a second end;
   a needle holder formed with a means for removably attaching said needle to said syringe body to place said second end of said needle in fluid communication with said chamber;
   a sheath positioned over said needle, said sheath slideably mounted to said needle holder for movement relative thereto between a first configuration wherein said sheath covers said first end of said needle, and a second configuration wherein said sheath retracts over said needle to expose said first end of said needle;
   a lock mounted on said sheath, said lock having a locking tab to lock said sheath in said first configuration to prohibit relative movement between said sheath and said needle holder;
   a finger grip for moving said locking tab relative to said sheath to unlock said sheath to allow said sheath to move into said second configuration; and
   a plunger engageable with said chamber of said syringe body to expel medication from said chamber and through said needle.

2. A syringe as recited in claim 1 wherein said finger grip is slideably mounted on said syringe body to allow said sheath to be unlocked by movement of said finger grip relative to said syringe body.

3. A syringe as recited in claim 1 further comprising a means for biasing said sheath into said first configuration.

4. A syringe as recited in claim 3 wherein said biasing means comprises a spring enclosure mounted on said needle holder and a spring disposed within said spring enclosure.

5. A syringe as recited in claim 1 wherein said needle holder is formed with a cylindrical section, said cylindrical section being positioned over said second end of said needle and extending proximal thereto to cover said second end of said needle.

6. A syringe as recited in claim 1 wherein said first end of said needle extends substantially along a first axis and said second end of said needle extends substantially along a second axis, said second axis being substantially parallel to said first axis and distanced therefrom.

7. A syringe assembly as recited in claim 6 wherein said sheath is substantially cylindrically shaped and said syringe further comprises a means for maintaining said sheath substantially centered on said first axis.

8. A syringe as recited in claim 4 wherein said lock is formed with a lock body and said locking tab extends from said lock body to create a hinged connection between said locking tab and said lock body, said lock body being attached to said sheath with said locking tab being for engagement with said spring enclosure to prohibit distal movement of said sheath relative to said needle holder.

9. A syringe as recited in claim 4 wherein said needle, said needle holder, said sheath, said spring enclosure, said spring and said locking tab are assembled into an integral cartridge assembly that can be removably attached to said syringe body by attaching said needle holder to said syringe body.

10. A syringe which comprises:
    a syringe body having a chamber for holding a medicament;
    a needle having a first end for releasing fluid and a second end for receiving fluid from said chamber;
    a sheath slideably mounted on said needle for movement relative thereto, with a hinged tab extending from said sheath for movement relative to said sheath between a first configuration to prohibit relative movement between said sheath and said needle and a second configuration to allow relative movement between said sheath and said needle;
    a finger grip slideably mounted on said syringe body, said finger grip being formed with a tang for biasing said tab into said second configuration to allow relative movement between said sheath and said needle; and
    a plunger engageable with said chamber of said syringe body to expel a portion of said medicament from said chamber and through said needle.

11. A syringe as recited in claim 10 further comprising a means for biasing said sheath into said first configuration.

12. A syringe as recited in claim 11 wherein said biasing means comprises a spring enclosure attached to said needle and a spring disposed within said spring enclosure.

13. A syringe as recited in claim 10 wherein said first end of said needle extends substantially along a first axis and said second end of said needle extends substantially along a second axis, said second axis being substantially parallel to said first axis and distanced therefrom.

14. A syringe assembly as recited in claim 13 wherein said sheath is substantially cylindrically shaped and said syringe further comprises a means or maintaining said sheath substantially centered on said first axis.

15. A method for using a syringe comprising the steps of:
    providing a syringe body having a chamber holding a fluid medication;
    slideably mounting a finger grip formed with a distal end onto said syringe body, said finger grip formed with a tang extending away from said syringe body at said distal end of said finger grip;

providing a needle cartridge having a needle formed with a first end and a second end, a needle holder for holding said needle, a sheath slideably mounted to said needle holder and locked in a position over said first end of said needle by a locking tab extending from said sheath, said locking tab attached to said sheath to create a hinged connection therebetween;

attaching said needle cartridge to said syringe body to place said second end of said needle in fluid communication with said chamber;

rotating said needle cartridge relative to said syringe body to align said tang into a position that is adjacent and distal to said locking tab; and sliding said finger grip relative to said syringe body to contact said locking tab with said tang and pivot said locking tab relative to said sheath and about said hinge connection to unlock said sheath and allow movement of said sheath relative to said needle.

16. A method as recited in claim 15 further comprising the step of:

inserting said first end of said needle into a patient.

17. A method as recited in claim 16 further comprising the step of:

depressing a plunger into said chamber of said syringe body to expel medication from said chamber and through said needle.

18. A method as recited in claim 17 further comprising the steps of:

withdrawing said first end of said needle from said patient; and releasing said finger grip to move said sheath over said first end of said needle and lock said sheath over said first end of said needle.

19. A method as recited in claim 18 further comprising the step of:

detaching said needle cartridge from said syringe body.

20. A method as recited in claim 19 further comprising the step of:

autoclaving said syringe body for reuse.

* * * * *